United States Patent
Newmark et al.

(10) Patent No.: US 10,966,959 B2
(45) Date of Patent: Apr. 6, 2021

(54) USE OF A ROTIFER-DERIVED COMPOUND AND ITS ANALOGS FOR PREVENTING SCHISTOSOMIASIS

(71) Applicant: Wisconsin Alumni Research Foundation, Madison, WI (US)

(72) Inventors: Phillip A. Newmark, Madison, WI (US); Jonathan V. Sweedler, Urbana, IL (US); Ning Yang, Urbana, IL (US); Jiarong Gao, Madison, WI (US); Peter Yau, Urbana, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/445,766

(22) Filed: Jun. 19, 2019

(65) Prior Publication Data

US 2019/0381006 A1    Dec. 19, 2019

Related U.S. Application Data

(60) Provisional application No. 62/687,027, filed on Jun. 19, 2018.

(51) Int. Cl.
| | | |
|---|---|---|
| *A61K 31/407* | (2006.01) | |
| *A61K 9/00* | (2006.01) | |
| *A61K 31/4985* | (2006.01) | |
| *A61P 33/12* | (2006.01) | |

(52) U.S. Cl.
CPC .......... *A61K 31/407* (2013.01); *A61K 9/0014* (2013.01); *A61K 31/4985* (2013.01); *A61P 33/12* (2018.01)

(58) Field of Classification Search
CPC .................................................. A61K 31/407
See application file for complete search history.

(56) References Cited

FOREIGN PATENT DOCUMENTS

| WO | WO-0059909 A1 * | 10/2000 | ............. A61P 25/24 |
|---|---|---|---|
| WO | WO00/59909 | 12/2000 | |

OTHER PUBLICATIONS

Stirewalt M & Lewis FA (1981) *Schistosoma mansoni*: effect of rotifers on cercarial output, motility and infectivity. *Int J Parasitol* (4):301-308; 66 pages.

\* cited by examiner

*Primary Examiner* — Svetlana M Ivanova
(74) *Attorney, Agent, or Firm* — Foley & Lardner LLP

(57) ABSTRACT

The present disclosure relates provides compounds according to Formula I or Formula II as well as compositions including such compounds useful for the prevention of schistosomiasis infection and/or swimmer's itch.

11 Claims, 11 Drawing Sheets

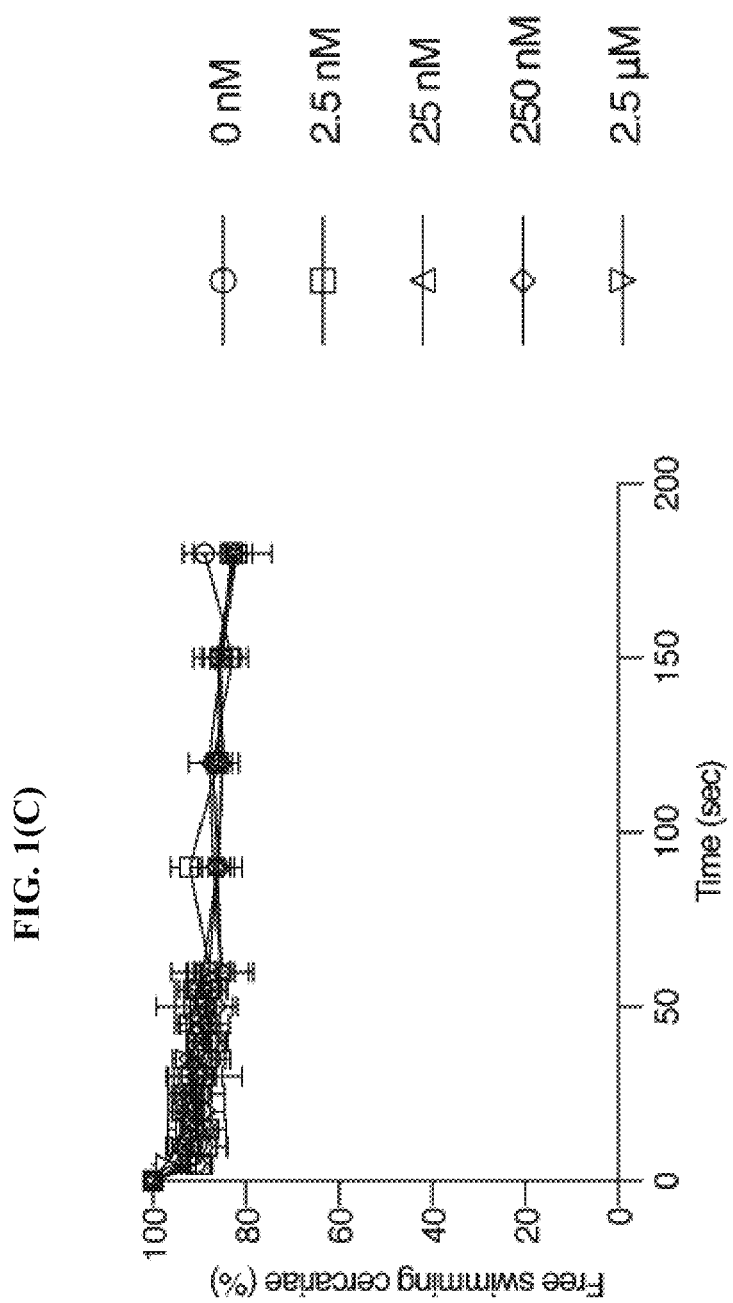
FIG. 1(C)
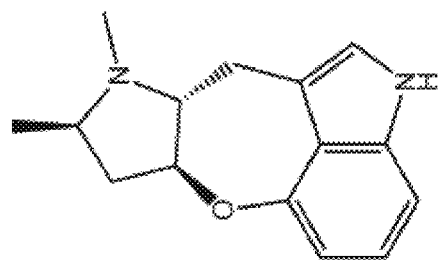

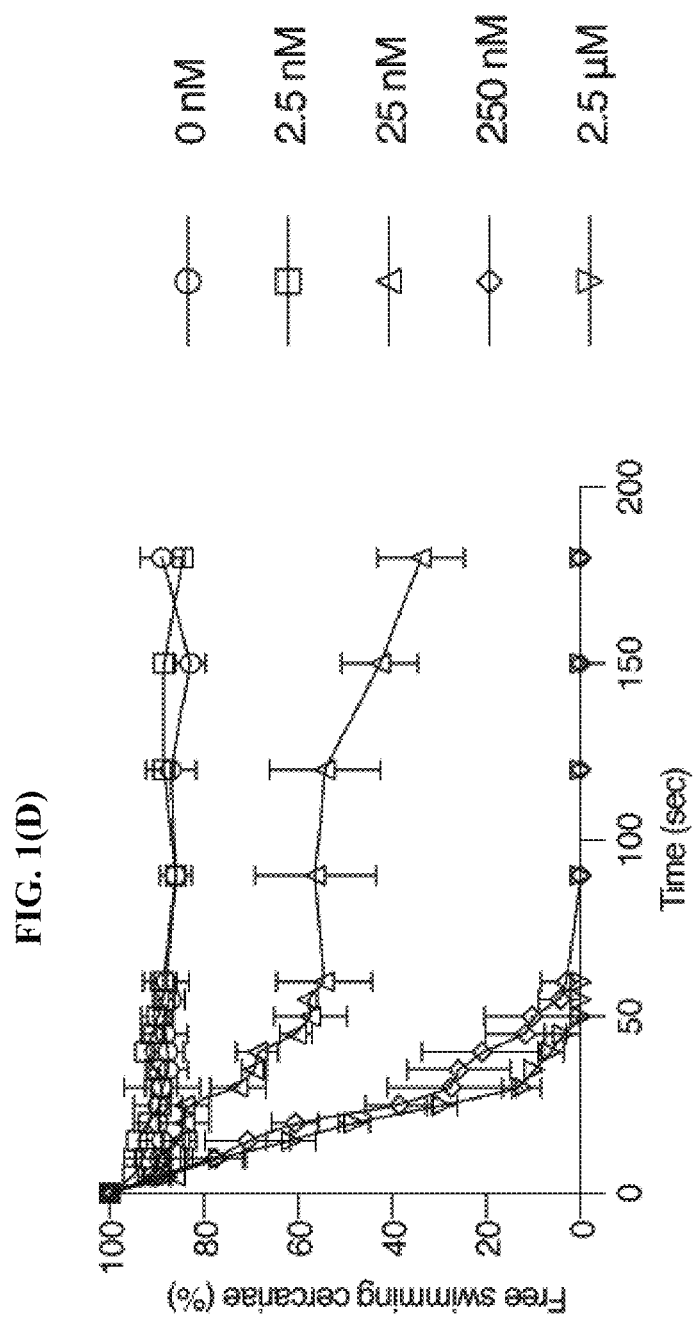
FIG. 1(D)
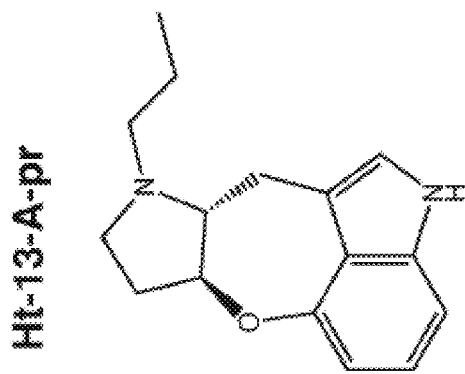

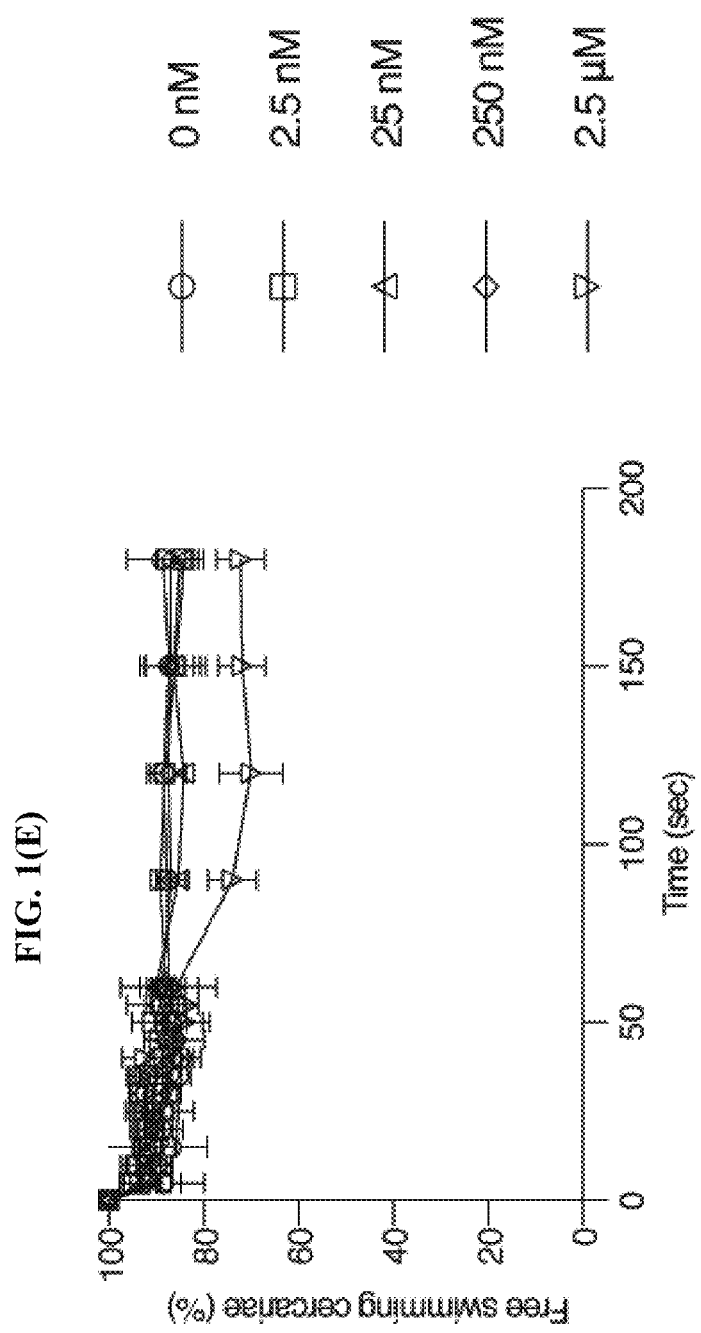
FIG. 1(E)
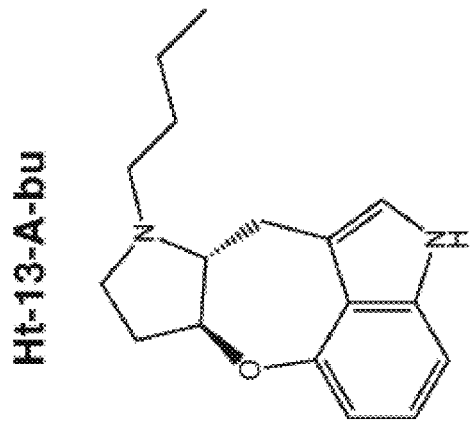

USE OF A ROTIFER-DERIVED COMPOUND AND ITS ANALOGS FOR PREVENTING SCHISTOSOMIASIS

CROSS-REFERENCE TO RELATED APPLICATIONS

This application claims the benefit of U.S. Provisional Application No. 62/687,027 filed Jun. 19, 2018, which is incorporated herein by reference in its entirety.

STATEMENT OF GOVERNMENT SUPPORT

This invention was made with government support under DA018310 and AI099642 awarded by the National Institutes of Health. The government has certain rights in the invention.

TECHNICAL FIELD

The present technology relates generally to a class of tetracyclic alkaloid compounds, including an oxepineindole framework fused with a pyrrolidine ring. The present disclosure also includes pharmaceutical compositions and methods of use thereof. Specifically, the compounds and compositions of the present technology are useful in preventing schistosomiasis and swimmer's itch.

BACKGROUND

The following description of the background of the present technology is provided simply as an aid in understanding the present technology and is not admitted to describe or constitute prior art to the present technology.

Schistosomiasis is caused by the blood fluke *Schistosoma*. The life cycle of schistosomes shifts between an intermediate snail host and a mammalian definitive host. Once shed from snails, infectious larvae of the schistosomes, called cercariae, infect humans by swimming in freshwater sources and burrowing under the skin. The cercariae lose their tails while burrowing through the skin of the host, becoming schistosomulae. The schistosomulae migrate through the bloodstream to the hepatic portal vein to mature to adult worms where the females lay eggs, and the cycle repeats. Schistosomiasis is a devastating and widespread disease affecting more than 200 million people worldwide. Current treatment relies on the drug, Praziquantel, for which there is evidence of increasing drug resistance. Recent efforts to develop a vaccine to combat schistosomiasis have proven unsuccessful.

SUMMARY

In an aspect, a method for preventing schistosomiasis is provided, where the method includes administering to a subject at risk of schistosomiasis infection, an effective amount of a compound of Formula I,

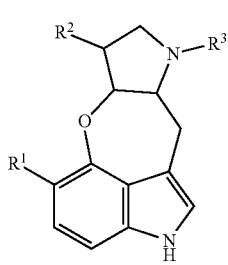

(I)

or stereoisomer, tautomer, and/or a pharmaceutically acceptable salt thereof, where $R^1$ is H, OH, or $C_1$-$C_3$ alkoxy; $R^2$ is H or $C_1$-$C_3$ alkyl; and $R^3$ is H or $C_1$-$C_3$ alkyl.

In an aspect, a method for preventing swimmer's itch is provided, where the method includes administering to a subject at risk of contracting swimmer's itch, an effective amount of a compound of Formula I.

In an aspect, a pharmaceutical composition is provided, comprising an effective amount, for the prevention of schistosomiasis infection or swimmer's itch, of a compound of Formula II,

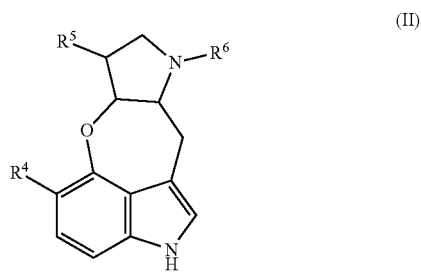

(II)

or stereoisomer, tautomer, and/or a pharmaceutically acceptable salt thereof, where $R^4$ is OH, or $C_1$-$C_3$ alkoxy; $R^5$ is H or $C_1$-$C_3$ alkyl; $R^6$ is H or $C_1$-$C_3$ alkyl, and a pharmaceutically acceptable carrier or excipient.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1(C) shows the percentage of cercariae (~50) continuing to swim over three minutes after addition of Ht-13-B at the specified final concentrations, according to the Examples. Triplicates were performed. Data are mean±S.D.

FIG. 1(D) shows the percentage of cercariae (~50) continuing to swim over three minutes after addition of Ht-13-A-pr at the specified final concentrations, according to the Examples. Triplicates were performed. Data are mean±S.D.

FIG. 1(E) shows the percentage of cercariae (~50) continuing to swim over three minutes after addition of Ht-13-A-bu at the specified final concentrations, according to the Examples. Triplicates were performed. Data are mean±S.D.

DETAILED DESCRIPTION

Figure 1A:
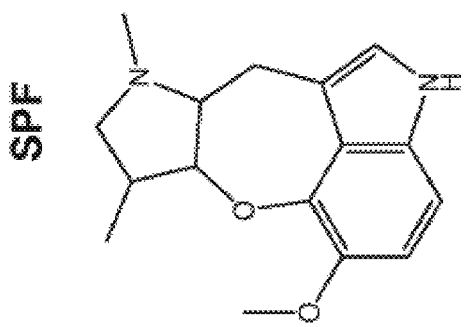
FIG. 1(A) shows the percentage of cercariae (~50) continuing to swim over three minutes after addition of SPF at the specified final concentrations, according to the Examples. Triplicates were performed. Data are mean±S.D.
Figure 1A:
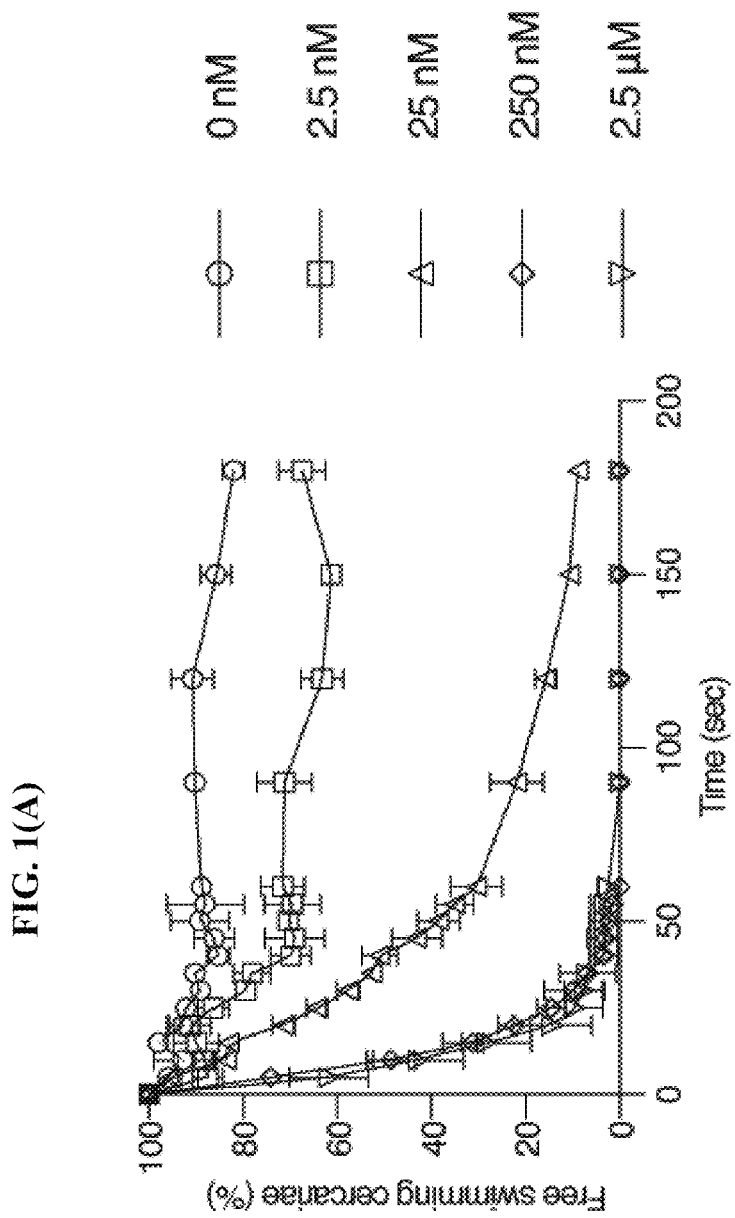

The definitions of certain terms as used in this specification are provided below. Unless defined otherwise, all technical and scientific terms used herein generally have the same meaning as commonly understood by one of ordinary skill in the art to which the present technology belongs.

The following terms are used throughout as defined below.

As used herein and in the appended claims, singular articles such as "a", "an", and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "schistosomiasis" refers to a parasitic disease caused by an infection of trematodes of the genus *Schistosoma*.

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

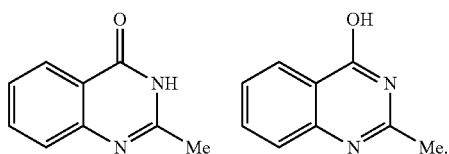

As another example, guanidines may exhibit the following isomeric forms in protic organic solution, also referred to as tautomers of each other:

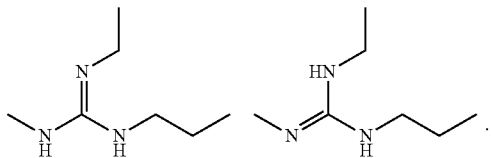

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or pharmaceutical compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include, but are not limited to, halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, $C_m$-$C_n$, such as $C_1$-$C_{12}$, $C_1$-$C_6$, or $C_1$-$C_3$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 3 carbon atoms. Examples of straight chain alkyl groups include, but are not limited to, groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, amino alkyl, alkylaminoalkyl, dialkylaminoalkyl, alkoxyalkyl, carboxyalkyl, and the like.

Alkoxy groups are hydroxyl groups (—OH) in which the bond to the hydrogen atom is replaced by a bond to a carbon atom of a substituted or unsubstituted alkyl group as defined above. Examples of linear alkoxy groups include, but are not limited to, methoxy, ethoxy, propoxy, butoxy, pentoxy, hexoxy, and the like. Examples of branched alkoxy groups include, but are not limited to, isopropoxy, sec-butoxy, tert-butoxy, isopentoxy, isohexoxy, and the like. Examples of cycloalkoxy groups include, but are not limited to, cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The term "hydroxyl" as used herein can refer to —OH or its ionized form, —O⁻.

The present technology provides pharmaceutical compositions and medicaments comprising any of one of the embodiments of the compounds (drugs) disclosed herein and a pharmaceutically acceptable carrier or one or more excipients. The pharmaceutical compositions may be used in the methods and preventative treatments described herein. The pharmaceutical compositions may include an effective amount of any of one of the embodiments of the compounds of the present technology disclosed herein. In any of the above embodiments, the effective amount may be determined in relation to a subject. "Effective amount" refers to the amount of a compound or pharmaceutical composition required to produce a desired therapeutic and/or prophylactic effect. In the context of therapeutic or prophylactic applications, the amount of a compound or a composition administered to the subject will vary depending on the composition, the degree, type, and severity of the infection or risk of infection and on the characteristics of the individual. One example of an effective amount includes amounts or dosages that yield acceptable toxicity and bioavailability levels for therapeutic (pharmaceutical) use including, but not limited to, the prevention or reduction of schistosomiasis infection or swimmer's itch. As used herein, a "subject" or "patient" is a mammal, such as a cat, dog, rodent or primate. Typically the subject is a human, and, preferably, a human suffering from an infection with a *Schistosoma* sp. sensitive to the compounds and pharmaceutical compositions of the present technology, i.e., a schistosomiasis infection capable of treatment with an effective amount of the compounds and compositions of the present technology. The term "subject" and "patient" can be used interchangeably.

As used herein, the "administration" of a compound or pharmaceutical composition to a subject includes any route of introducing or delivering to a subject an effective amount of a compound or pharmaceutical composition of the present technology to perform its intended function. Administration can be carried out by any suitable route, including but not limited to, topical administration. Administration includes self-administration and the administration by another.

"Treating" within the context of the instant technology, means alleviation, in whole or in part, of symptoms, for example the symptoms of schistosomiasis and/or swimmer's itch herein, associated with a disorder or disease, or slowing, inhibition or halting of further progression or worsening of those symptoms, or prevention or prophylaxis of the disease or disorder in a subject at risk for developing the disease or disorder. In the present context, "preventing" means the prevention in whole or in part of the infection, condition, or disease being prevented, including at least one symptom associated therewith or caused thereby.

The present disclosure is directed to a tetracyclic alkaloid compounds that advantageously paralyze the cercariae at nanomolar concentrations. Without wishing to be bound by theory, it is believed that one therapeutic approach to preventing schistosomiasis infection includes immobilizing and/or eliminating the cercariae from the fresh water.

In one aspect, the present disclosure provides compounds useful for the prevention of schistosomiasis infection or swimmer's itch, such as those caused by *Schistosoma* sp. and/or *Trichobilharzia* sp. Thus, for example, the present technology provides compounds of Formula I:

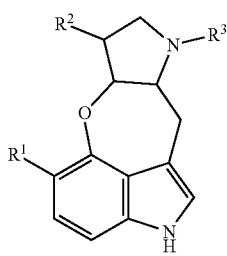

(I)

and stereoisomers, tautomers, and/or pharmaceutically acceptable salts thereof, wherein $R^1$ is H, OH, or $C_1$-$C_3$ alkoxy; $R^2$ is H or $C_1$-$C_3$ alkyl; and $R^3$ is H or $C_1$-$C_3$ alkyl.

In some embodiments, the compound of Formula I is a compound isolated from *Rotaria rotatoria*, and has the chemical formula $C_{16}H_{20}N_2O_2$, also known as Schistosome Paralysis Factor (SPF). In some embodiments, SPF is 5-methoxy-7,9-dimethyl-6a,7,8,9,9a,10-hexahydro-2H-pyrrolo[2',3':6,7]oxepino[4,3,2-cd]indole and has the following structure:

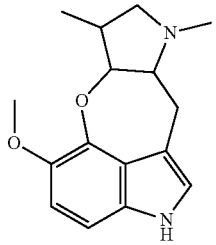 [SMILES: COc1ccc2[nH]cc3c2c1OC1C(C)CN(C)C1C3]

Further provided are salts of SPF, including but not limited to, pharmaceutical salts thereof.

In one aspect, the present disclosure provides a method of preventing schistosomiasis in a subject, wherein the method comprises administering to the subject at risk of schistosomiasis infection, an effective amount of a compound of Formula I, a stereoisomer, a tautomer, a pharmaceutically acceptable salt thereof, or a mixture of any two or more thereof. The compound of Formula I, stereoisomers, tautomers, and/or salts may be topically administered or administered by another suitable route. Additionally or alternatively, in some embodiments of the method, the infection is caused by *Schistosoma* sp. Additionally or alternatively, in some embodiments of the method, the infection is caused by *Schistosoma haematobium, Schistosoma intercalatum, Schistosoma japonicum, Schistosoma mansoni, Schistosoma mekongi*, or a combination of any two or more thereof.

Additionally or alternatively, in some embodiments of the method of preventing schistosomiasis, the effective amount comprises a concentration of the compound of about 25 nM to about 250 μM. Additionally or alternatively, in some embodiments, the effective amount comprises a concentration of the compound of about 25 nM, about 30 nM, about 35 nM, about 40 nM, about 45 nM, about 50 nM, about 60 nM, about 70 nM, about 80 nM, about 90 nM, about 100 nM, about 125 nM, about 150 nM, about 175 nM, about 200 nM, about 250 nM, about 300 nM, about 350 nM, about 400 nM, about 450 nM, about 500 nM, about 750 nM, about 1 μM, about 2 μM, about 3 μM, about 4 μM, about 5 μM, about 10 μM, about 15 μM, about 20 μM, about 25 μM, about 50 μM, about 75 μM, about 100 μM, about 150 μM, about 200 μM, about 250 μM, or any range including and/or in between any two of these values.

In one aspect, the present disclosure provides a method of preventing swimmer's itch in a subject, wherein the method comprises administering to the subject at risk of contracting swimmer's itch, an effective amount of a compound of Formula I, a stereoisomer, a tautomer, a pharmaceutically acceptable salt thereof, or a mixture of any two or more thereof. The compound of Formula I, stereoisomers, tautomers, and/or salts may be topically administered or administered by another suitable route. Additionally or alternatively, in some embodiments of the method, the swimmer's itch is caused by other schistosome species whose definitive hosts are birds or non-human mammals, including *Trichobilharzia* sp., *Gigantobilharzia* sp., *Austrobilharzia* sp., or a combination thereof. Additionally or alternatively, in some embodiments of the method, the swimmer's itch is caused by *Trichobilharzia physellae, Trichobilharzia stagnicolae*, or a combination thereof.

Additionally or alternatively, in some embodiments of the method of preventing swimmer's itch, the effective amount comprises a concentration of the compound of about 25 nM to about 250 μM. Additionally or alternatively, in some embodiments, the effective amount comprises a concentration of the compound of about 25 nM, about 30 nM, about 35 nM, about 40 nM, about 45 nM, about 50 nM, about 60 nM, about 70 nM, about 80 nM, about 90 nM, about 100 nM, about 125 nM, about 150 nM, about 175 nM, about 200 nM, about 250 nM, about 300 nM, about 350 nM, about 400 nM, about 450 nM, about 500 nM, about 750 nM, about 1 μM, about 2 μM, about 3 μM, about 4 μM, about 5 μM, about 10 μM, about 15 μM, about 20 μM, about 25 μM, about 50 μM, about 75 μM, about 100 μM, about 150 μM, about 200 μM, about 250 μM, or any range including and/or in between any two of these values.

Specific dosages employed in any of the methods disclosed herein may be adjusted depending on conditions of infection, the age, body weight, general health conditions, sex, and diet of the subject, dose intervals, administration routes, excretion rate, and combinations of drugs.

In any embodiment disclosed herein, the compounds disclosed herein may be isolated and used at various purities, e.g., a purity of at least 60%, at least 70%, at least 80%, at least 90%, at least 95%, at least 96%, at least 97%, at least 98%, at least 99%, or at least 99.5%.

In any embodiment disclosed herein, the subject is a mammal, e.g., a human, a monkey, a chimpanzee, an ape, a cat, a dog, a pig, a mouse, a rat, a horse, or a sheep. Additionally or alternatively, in some embodiments of the method, the subject is a human.

In one aspect, the present disclosure provides a pharmaceutical composition comprising a compound of Formula II:

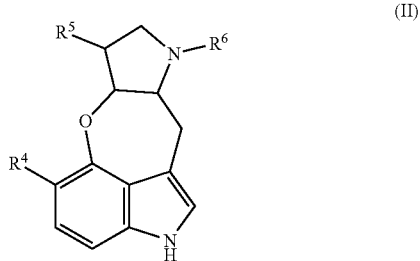

(II)

or stereoisomer, tautomer, and/or pharmaceutically acceptable salt thereof, wherein $R^4$ is OH, or $C_1$-$C_3$ alkoxy; $R^5$ is H or $C_1$-$C_3$ alkyl; and $R^6$ is H or $C_1$-$C_3$ alkyl, and a pharmaceutically acceptable carrier or excipient. Pharmaceutical compositions of the present disclosure may be formulated for topical administration.

In one aspect, the present disclosure provides a pharmaceutical composition comprising an effective amount of a compound of Formula II, for the prevention of schistosomiasis infection and/or swimmer's itch in a subject. Additionally or alternatively, in some embodiments, the schistosomiasis infection is caused by Schistosoma sp. Additionally or alternatively, in some embodiments, the infection is caused by Schistosoma haematobium, Schistosoma intercalatum, Schistosoma japonicum, Schistosoma mansoni, Schistosoma mekongi, or a combination of any two or more thereof. Additionally or alternatively, in some embodiments, the swimmer's itch is caused by other schistosome species whose definitive hosts are birds or non-human mammals, including Trichobilharzia sp., Gigantobilharzia sp., Austrobilharzia sp., or a combination thereof. Additionally or alternatively, in some embodiments, the swimmer's itch is caused by Trichobilharzia physellae, Trichobilharzia stagnicolae, or a combination thereof.

Additionally or alternatively, in some embodiments, the effective amount for prevention of schistosomiasis infection or swimmer's itch, comprises a concentration of the compound of about 25 nM to about 250 μM. Additionally or alternatively, in some embodiments, the effective amount comprises a concentration of the compound of about 25 nM, about 30 nM, about 35 nM, about 40 nM, about 45 nM, about 50 nM, about 60 nM, about 70 nM, about 80 nM, about 90 nM, about 100 nM, about 125 nM, about 150 nM, about 175 nM, about 200 nM, about 250 nM, about 300 nM, about 350 nM, about 400 nM, about 450 nM, about 500 nM, about 750 nM, about 1 μM, about 2 μM, about 3 μM, about 4 μM, about 5 μM, about 10 μM, about 15 μM, about 20 μM, about 25 μM, about 50 μM, about 75 μM, about 100 μM, about 150 μM, about 200 μM, about 250 μM, or any range including and/or between any two of these values.

Specific dosages may be adjusted depending on conditions of infection, the age, body weight, general health conditions, sex, and diet of the subject, dose intervals, administration routes, excretion rate, and combinations of drugs.

In any embodiment disclosed herein, the subject is a mammal, e.g., a human, a monkey, a chimpanzee, an ape, a cat, a dog, a pig, a mouse, a rat, a horse, or a sheep. Additionally or alternatively, in some embodiments of the method, the subject is a human.

Additionally or alternatively, in some embodiments, the pharmaceutical composition may comprise a pharmaceutically acceptable excipient. Exemplary pharmaceutically acceptable excipients include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, silicone adhesives, as well as a combination of any two or more thereof.

The present pharmaceutical compositions may be formulated for topical administration on their own or may be incorporated into consumer skincare formulations such as sunscreens, moisturizing lotions, skin conditioners and the like.

Formulations

As noted herein, the present technology provides pharmaceutical compositions that include an effective amount of SPF, a compound of Formula I, a compound of Formula II, a stereoisomer, tautomer and/or pharmaceutically acceptable salt thereof, or a mixture of any two or more thereof.

The pharmaceutical compositions may be prepared by mixing one or more compounds of the present technology, and/or pharmaceutically acceptable salts thereof, with pharmaceutically acceptable carriers, excipients, binders, diluents or the like to prevent infections, such as schistosomiasis and swimmer's itch, associated with Schistosoma sp., Trichobilharzia sp., Gigantobilharzia sp., or Austrobilharzia sp. The instant compositions can be formulated for various routes of administration, for example, by topical administration. The following dosage forms are given by way of example and should not be construed as limiting the instant present technology.

Dosage forms for the topical or transdermal administration of compounds of the present disclosure include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

The pharmaceutical compositions of the present disclosure may be designed to be short-acting, fast-releasing, long-acting, and sustained-releasing as described below. Thus, the pharmaceutical compositions may also be formulated for controlled release or for slow release.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

EXAMPLES

The present technology is further illustrated by the following examples, which should not be construed as limiting in any way.

Example 1: Experimental Methods

Artificial Pond Water

Four stock solutions were prepared to make artificial pond water: 1) 0.25 g/L $FeCl_3$ $6H_2O$, 2) 12.9 g/L $CaCl_2).2H_2O$, 3) 10 g/L $MgSO_4.7H_2O$, and 4) 34 g/L $KH_2PO_4$ 1.5 g/L $(NH_4)_2SO_4$, pH 7.2. For 1 L artificial pond water, a total of 0.5 mL of $FeCl_3$ solution, 2.5 mL $CaCl_2$) solution, 2.5 mL $MgSO_4$ solution and 1.25 mL phosphate buffer were added.

Obtaining S. mansoni Cercariae and Miracidia

Infected B. glabrata snails provided by Biomedical Research Institute (BRI, Rockville, Md.) were maintained in artificial pond water and fed Layer Crumbles (chicken feed) (Rural King, Mattoon, Ill.). To obtain S. mansoni cercariae, B. glabrata snails were exposed to light at 26° C. for 1-2 hrs. Artificial pond water containing cercariae was passed through 100 μm cell strainer (Falcon, Corning Inc., Corning, N.Y.) to remove snail food and feces. Cercariae were then collected using custom-made 20 μm cell strainers.

Rotifer Culture

Since both rotifer species reproduce parthenogenetically, we clonally expanded each species into one-liter cultures from a single rotifer. Individual rotifers (R. rotatoria and P. acuticornis) were initially isolated from the shell of B. glabrata and cultured in artificial pond water. Each individual colony was expanded and maintained in one liter flasks. Both species were fed with Roti-rich liquid invertebrate food (Florida Aqua Farms Inc., Dade City, Fla.). Rotifer-conditioned water was collected every month by filtering out the rotifers using 20 μm cell strainer. Filtered rotifers were used to establish new cultures.

Crude Rotifer-Conditioned Water Preparation

One liter rotifer media was lyophilized, reconstituted with 50 mL $dH_2O$ and filtered through 10,000 and 650 (MWCO) Pall Minimate TFF Capsules with Omega membrane (Ann Arbor, Mich.). Filtrate (<650 Da) was freeze dried. For RP-HPLC, 300 mg of the dried material was dissolved in $dH_2O$ and run on a RP-HPLC-Merck Chromolith semi-prep RP-18e column (Darmstadt, Germany) at 5 ml/min using a gradient of 100% A to 60% B in 60 minutes. 10 mL fractions were collected and assayed for biological activity. Fractions containing biological activity were saved for further study. Solvent A, $H_2O$; solvent B, acetonitrile.

Further Purification of Rotifer Media

The bioactive fractions were pooled, freeze dried with SpeedVac (Savant, Thermo Fisher Scientific, Waltham, Mass.), reconstituted with 500 μL $dH_2O$ and injected into a 4.6 mm diameter×25 cm Symmetry column (Waters Corp., Milford, Mass.). Breeze2 analytical LC system (Waters) was employed for separation at 0.5 ml/min with the following solvents and gradients: Solvent A, 0.1% formic acid (FA); solvent B, methanol with 0.1% FA; 0-10 min 0-10% B, 10-30 min 10-35% B, 30-33 min 35-80% B, 33-37 min 80-80% B, 37-40 min 80-0% B. Eluents were collected manually based on peak elution. All fractions were lyophilized, reconstituted with water and analyzed with MALDI-MS. Fractions containing biological activity were saved for future use.

Matrix-Assisted Laser Desorption/Ionization Mass Spectrometry (MALDI-MS) Analysis For each collected fraction, 1 μL of sample solution was spotted on ground steel MALDI target and mixed with 1 μL of alpha-cyano-4-hydroxy-cinnamic acid (CHCA, Sigma-Aldrich, MO) solution (10 mg/mL CHCA in 50% acetonitrile solution with 0.005% trifluoroacetic acid). Mass calibration, spectra acquisition and analysis were performed under conditions as previously described (see Tillmaand et al., *J. Am. Soc. Mass Spectrom.*, 2015, 26:2051-2061).

High-Resolution Quadrupole Time-of-Flight Mass Spectrometry (Q-TOF MS) Analysis

1 μL of the bioactive fractions was separated on a Magic 0.1×150 mm column (Michrom, Calif.) and analyzed with maXis 4G mass spectrometer (Bruker, Mass.) using previously established method for metabolite study (see Aerts et al., *Anal. Chem.*, 2014, 86:3203-3208). The separation was performed at 300 nl/min by use of solvent A (95% water, 5% acetonitrile with 0.1% FA) and solvent B (5% water, 95% acetonitrile with 0.1% FA) with the following gradient conditions: 0-5 min 4% B, 5-50 min 4-50% B, 50-52 min 50-90% B, 52-60 min 90% B, 60-70 min 90-4% B, 70-90 min 4% B.

Hydrogen/Deuterium (H/D) Exchange Analysis

Acidified deuterated methanol ($CD_3OD$, methanol-d4, Sigma-Aldrich, St. Louis, Mo.) was made by adding 1 μL of deuterated FA into 1 mL of $CD_3OD$. 2 μL of the bioactive fractions were added into 18 μL of acidified methanol above. 15 μL of the mixture were analyzed by direct infusion into an 11 Tesla FTMS (Thermo Fisher Scientific) through NanoMate robot (Advion Inc., Ithaca, N.Y.). Full spectra were acquired with resolution set at 100 k.

Nuclear Magnetic Resonance (NMR) Analysis

Purified bioactive materials were dissolved in 250 μL of $CD_3OD$ and transferred into a 5 mm Shigemi NMR tube with a glass magnetic plug with susceptibility matched to $CD_3OD$ on the bottom. All NMR data were collected at 40° C. on an Agilent VNMRS 750 MHz spectrometer equipped with a 5 mm Varian indirect detection probe with z gradient capability. Collected NMR data included 1H spectrum, gradient selected correlation spectroscopy (gCOSY), total correlation spectroscopy (TOSCY), nuclear overhauser enhancement spectroscopy (NOESY) with a mixing time of 500 ms, heteronuclear single quantum coherence spectroscopy ($^1H$-$^{13}C$ HSQC) and heteronuclear multiple-bond correlation spectroscopy ($^1$H-$^{13}$C HMBC). The NMR spectra were analyzed using Mnova NMR software (Mestrelab Research, Spain).

Determination of SPF Concentration

The proton quantification experiments were performed at 23° C. on an Agilent 750 MHz VNMRS NMR spectrometer equipped with a 5 mm triple-resonance ($^1$H/$^{13}$C/$^{15}$N) indirect-detection probe with XYZ PFG gradient capability. The probe was calibrated using the qEstimate tool in the Agilent VnmrJ4.2 software with a known standard. The proton spectrum of the sample was collected with a 90-degree pulse angle of 8.5 ms, 16 scans and 10.4 seconds delay between scans. The Agilent VnmrJ4.2 software was used to determine the concentration of the sample based on the integration values of proton peaks. A total of 5 well-resolved proton peaks (7.12 ppm (1H), ~6.89 ppm (2H), 4.41 (1H), 3.83 (3H), and ~3.58 (2H)) was used, and the concentration of the sample was 1.55±0.07 mM. All concentrations used in the cercarial paralysis assay were diluted based on this value.

Cercarial Paralysis Assay

To capture the whole field while avoiding excess reflected light in a well, we used the lid of 96-well plate (Costar, Corning Inc., Corning, N.Y.). 40 μL of artificial pond water containing ~50 cercariae were added to each shallow well on the lid. 10 μL of SPF (dissolved in APW) was then added to reach the final concentration indicated. Using a high-speed camera (Olympus i-SPEED TR), attached to a stereomicroscope (Leica MZ125, Leica Microsystems, Wetzlar, Germany), we recorded cercariae movement at 20-60 fps at 1.25× magnification just prior to addition of test compounds until 3-4 minutes after treatment started. Raw movies were converted to .avi files using i-SPEED Viewer and compressed into JPEG format using ImageJ (addition of compound is considered time 0). We then counted the numbers of free swimming/paralyzed cercariae every 5 seconds for 1 minute and every 30 seconds thereafter for 3 minutes. The number of dead cercariae (those that never swim before and after SPF treatment) were subtracted from data. Experiments were performed in triplicate.

Mouse Infection Experiment

Mouse infections were performed by exposing mouse tails to *S. mansoni* cercariae according to standard protocol from BRI with slight modifications (see Lewis et al., *Curr. Protoc. Immunol.*, 2001, Chapter 19). Briefly, we secured mice in rodent restrainers (Thomas Scientific, Cat #551-BSRR) and put them vertically on top of a rack with grids. We pipetted 100 μL of each drug in proper concentration into a skinny glass tube (Fisher Scientific, Cat #14-958A) inside a 12×75 mm holding glass tube (VWR, Cat #47729-570). 300 μL of APW containing ~200 cercariae were pipetted into each skinny tube and incubated for 10 mins before we inserted mouse tail. Mouse tails were wiped with APW-moistened Kimwipes, inserted into the skinny tube, and exposed to cercariae for 30 mins. We sacrificed and perfused these mice six week-post infection. For each drug, we initially used three mice for controls (APW only) and three mice for each concentration tested except for 25 nM Ht-13-A and Ht-13-A-pr. We then repeated the experiments again with three mice for each condition. In addition, we included six mice for 25 nM Ht-13-A and Ht-13-A-pr so that we had six biological replicates total for each condition.

Adult worms were recovered by hepatic portal vein perfusion and briefly incubated in 2.5% Tricaine (Sigma) to separate males and females. We counted total numbers of adult worms under a stereomicroscope (Leica MZ75, Leica Microsystems). Livers from infected mice were fixed in 4% formaldehyde in PBS overnight. Largest liver lobes (left lobe) were submitted to University of Wisconsin-Madison Histology Core Facility for sectioning and Hematoxylin and Eosin staining. Each left lobe was evenly cut into 4-6 pieces and paraffin embedded on a large cassette. One slide (4-6 liver sections) for each liver was used for histological examination, which provided a representative view throughout the whole liver lobe. We took a tiled image of the whole slide using a Zeiss Axio Zoom microscope and used ImageJ (National Institutes of Health, Bethesda, Md.) to determine the area of each section. Total numbers of eggs in each section were counted and normalized to the area.

In adherence to the Animal Welfare Act and the Public Health Service Policy on Humane Care and Use of Laboratory Animals, all experiments with and care of mice were performed in accordance with protocols approved by the Institutional Animal Care and Use Committee (IACUC) of the University of Wisconsin-Madison (protocol approval number M005569).

Example 2: Identification of the Anti-Schistosomal Effects of *Rotaria rotatoria*

Previous reports have shown that rotifer colonization on snail shells significantly reduces cercariae output and motility. Two individual species of rotifers were isolated from snail shells, *Rotaria rotatoria* and *Philodina acuticornis*, and each species was confirmed via sequencing of the respective 18S rRNA. To determine if either rotifer species is responsible for the previously observed effects on the cercariae, 300 μL of *R. rotatoria*-conditioned artificial pond water (APW), cultured for one month, to 100 μL of APW containing freshly collected cercariae. Within five minutes, the addition of the rotifer-conditioned APW resulted in gradual paralysis of the cercariae, sinking to the bottom of the dish (data not shown). In contrast, no cercarial paralysis was observed with *P. acuticornis*-conditioned APW.

Example 3: Isolation and Purification of SPF from *Rotaria rotatoria*

To purify the cercarial paralyzing agent from the rotifers, molecular weight cut-off filtration (MWCO) was performed, followed by reversed-phase high-performance liquid chromatography (RP-HPLC) of the rotifer-conditioned water, with each collected fraction tested for paralytic activity on the cercariae. Paralysis of the cercariae was only observed from a peak eluting with a retention time ($t_R$) of 25-27 min. As expected, this peak was only detected in the *R. rotatoria*-conditioned water but not *P. acuticornis*-conditioned water. A second round of purification by HPLC resulted in a single peak with paralytic activity, with a $t_R$ of 24-26 min. Matrix-assisted laser desorption/ionization mass spectrometry (MALDI-MS) revealed a predominant signal of 273.16 Da (M+H) in this peak ($t_R$~24-26 min). Consistent with the paralysis assay, this signal (m/z 273.16) was exclusively detected in the fraction eluting at 24-26 min but not in the fractions before or after, suggesting that the m/z 273.16 was the cercarial paralyzing agent. Based on the biological activity, the *R. rotatoria*-derived compound was named "Schistosome Paralysis Factor" (SPF). High resolution quadrupole time-of-flight (Q-TOF) MS was used to determine the monoisotopic mass for protonated SPF, which was 273.1595 Da. These data suggest $C_{16}H_{20}N_2O_2$ as the best fitting formula for this molecule. Hydrogen/Deuterium exchange MS experiments demonstrate that there is one exchangeable proton in SPF, where the most dominant peak, m/z 275.1722, corresponded to deuterium singly charged SPF.

Example 4: Elucidation of the Chemical Structure of SPF

To determine the chemical structure of SPF, 0.126 mg of SPF was purified from 25 liters of *R. rotatoria*-conditioned water, and analyzed with 1D and 2D nuclear magnetic resonance (NMR). A novel tetracyclic structure was revealed by the 1H NMR results having 19 protons in the compound, which agreed with the best-fitting formula and Hydrogen/Deuterium exchange mass spectrometry (MS) analysis (Table 1). Heteronuclear single quantum coherence spectroscopy (HSQC) revealed three methyl, two methyl-

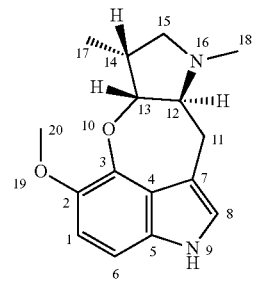

Compound B

TABLE 1

Summary of protons and carbons from 1H, COSY, HSQC, HMBC and NOESY.

| | $^{13}$C | | | $^{1}$H | | | | | |
|---|---|---|---|---|---|---|---|---|---|
| Position | δc (detected) | δc (predicted) | mult. | δH | Peak area | mult. | COSY | HMBC | NOESY |
| 1 | 116.8 | 110.4 | CH | 6.86 | 1.12 | d | 6 | 3, 5 | 18 |
| 2 | 143.1 | 148.2 | C | | | | | | |
| 3 | 143.7 | 143.1 | C | | | | | | |
| 4 | 120.6 | 120.3 | C | | | | | | |
| 5 | 138.1 | 132.5 | C | | | | | | |
| 6 | 106.6 | 103.7 | CH | 6.90 | 1.00 | d | 1 | 2, 4 | |
| 7 | 110.6 | 110.8 | C | | | | | | |
| 8 | 124.9 | 123.0 | CH | 7.09 | 1.00 | s | | 4, 5, 7 | 11, 11' |
| 9 | | | NH | | | | | | |
| 10 | | | O | | | | | | |
| 11 | 29.0 | 32.5 | CH$_2$ | 2.79 | | Overlap | 11', 12 | 7, 8, 12, 13 | 8, 11', 13 |
| 11' | 29.0 | 32.5 | CH$_2$ | 3.56 | 1.04 | dd | 11, 12 | 4, 7, 8, 12, 13 | 8, 11, 12 |
| 12 | 76.7 | 72.1 | CH | 3.10 | 1.16 | br | 11, 11', 13 | | 11', 13, 14, 17, 18 |
| 13 | 88.2 | 84.5 | CH | 4.40 | 1.05 | dd | 12, 14 | 3, 11, 15 | 11, 12, 14, 17 |
| 14 | 37.2 | 38.9 | CH | 2.77 | | Overlap | 13, 15', 17 | 15, 17 | 12, 13, 15', 17 |
| 15 | 65.8 | 62.6 | CH$_2$ | 2.70 | | Overlap | 15' | 12 | 15', 17 |
| 15' | 65.8 | 62.6 | CH$_2$ | 3.52 | 1.08 | dd | 14 | 12, 13 | 14, 15, 17, 18 |
| 16 | | | N | | | | | | |
| 17 | 14.0 | 14.6 | CH$_3$ | 1.34 | 3.01 | d | 14 | 13, 14, 15 | 12, 13, 14, 15, 15', 20 |
| 18 | 41.7 | 43.7 | CH$_3$ | 2.71 | | s | | 12, 15 | 12, 15' |
| 19 | | | O | | | | | | |
| 20 | 62.2 | 56.1 | CH$_3$ | 3.81 | 2.98 | s | | 2 | 17 | ene, six methine groups, and five quaternary carbons. Total correlation spectrometry (TOCSY) showed that aliphatic protons, except two methyl groups, are from one spin system. The connectivity of the neighboring groups was derived from correlation spectroscopy and heteronuclear multiple bond correlation (HMBC) spectra. Overall, the aliphatic region was composed of a dimethylpyrrolidine structure which is linked to an indole via a CH2 group and an oxygen. Nuclear Overhauser effect spectroscopy (NOESY) suggested (R, S, S) or (S, R, R) configurations on chiral centers. Altogether, combined NMR analysis led to two possible structures for SPF (Compound A and Compound B).

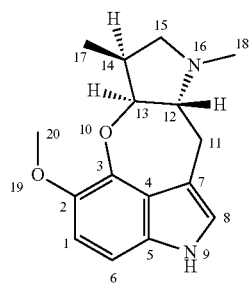

Compound A

Example 5: Quantification of Cercariae Paralysis in Response to SPF and Analogs

To determine if cercariae react to SPF or other analogs in a dose-dependent manner, serial dilutions of SPF were made in APW. To quantify the paralysis effect of SPF, the movement of the cercariae was recorded, as well as the number of free-swimming and non-swimming cercariae. In the absence of SPF, over 82% of cercariae were free-swimming over three minutes (FIG. 1(A)). In the presence of 2.5 nM SPF, the percentage of free-swimming cercariae dropped to 67% at three minutes post drug treatment. As the concentration of SPF increased, the rate of paralysis increased, and more cercariae were paralyzed at the end of the treatment. In the presence of 250 nM and 2.5 µM SPF, a maximum paralytic effect was observed, with the majority of cercariae paralyzed within 30 seconds.

Figure 1B:
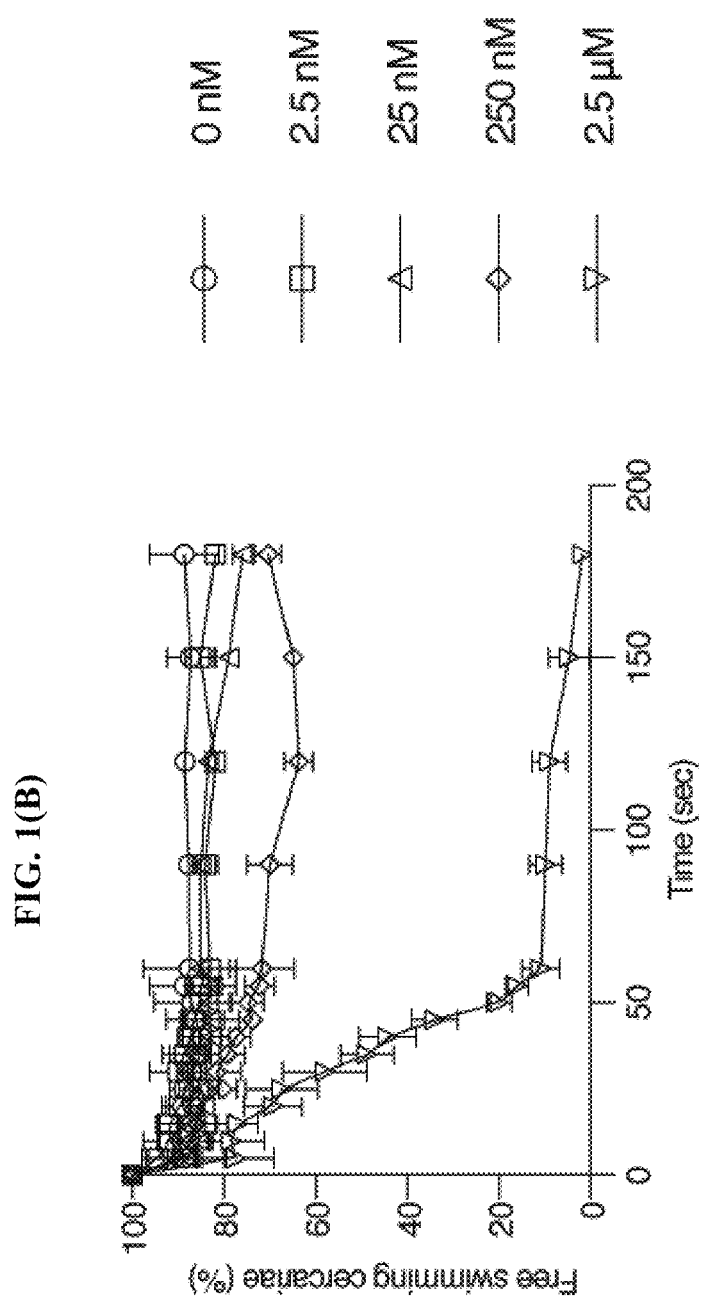
FIG. 1(B) shows the percentage of cercariae (~50) continuing to swim over three minutes after addition of Ht-13-A at the specified final concentrations, according to the Examples. Triplicates were performed. Data are mean±S.D.
Figure 1B:
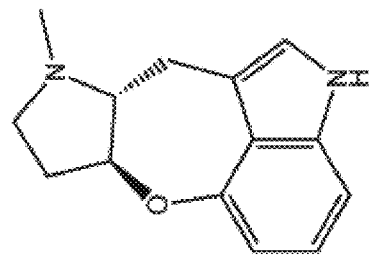

Based on the chemical structure of SPF, two structurally related natural compounds were found, Ht-13-A and Ht-13-B, which were originally isolated from *Streptomyces* sp. All three alkaloids share a novel oxepineindole framework fused with a pyrrolidine ring (FIG. 1(A)-1(C)). Although the total synthesis of SPF has not yet been achieved, total syntheses of Ht-13-A and Ht-13-B have been previously reported (see Zhang et al., *Tet. Lett.*, 2016, 57:2865-2867; Zhang et al., *J.*

Figure 1F:
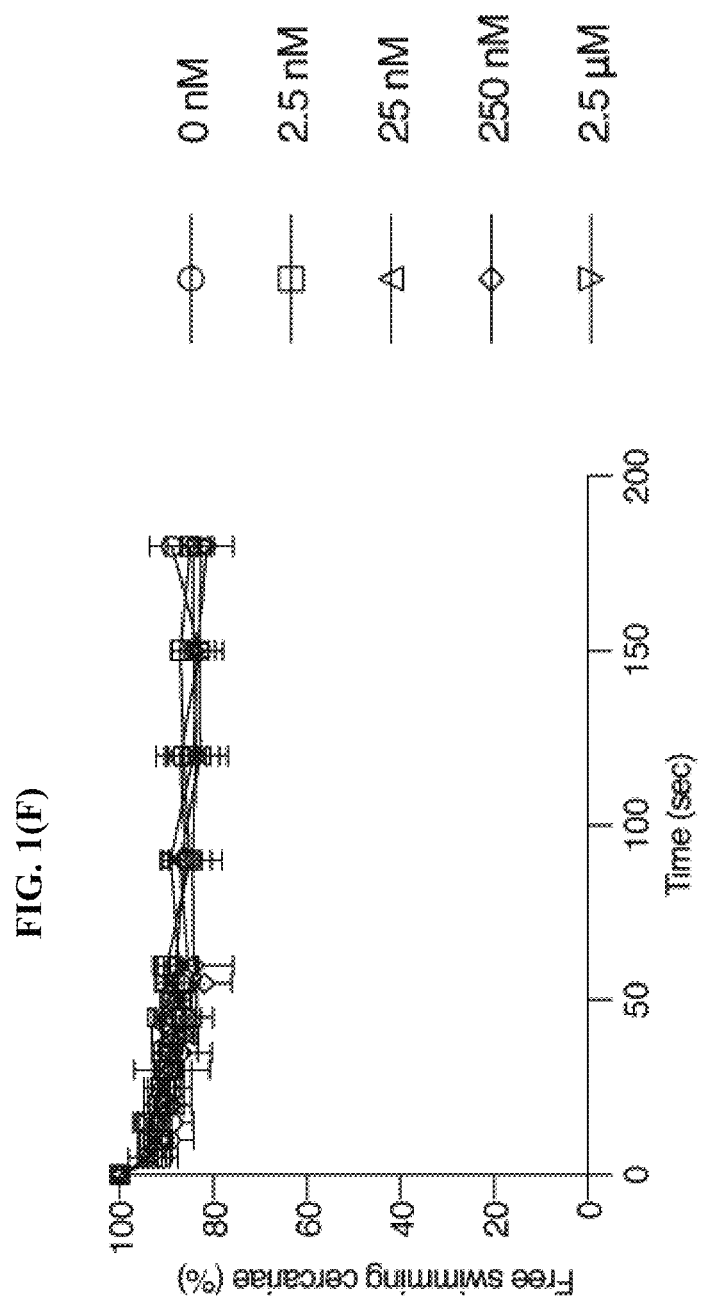
FIG. 1(F) shows the percentage of cercariae (~50) continuing to swim over three minutes after addition of Ht-13-A-bn at the specified final concentrations, according to the Examples. Triplicates were performed. Data are mean±S.D.
Figure 1F:
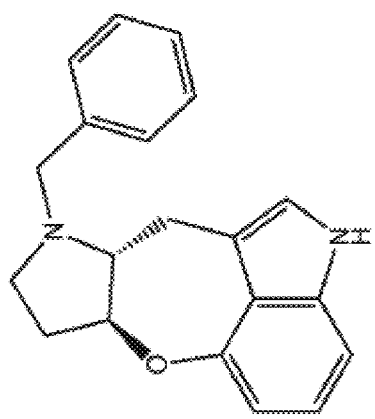
Figure 1G:
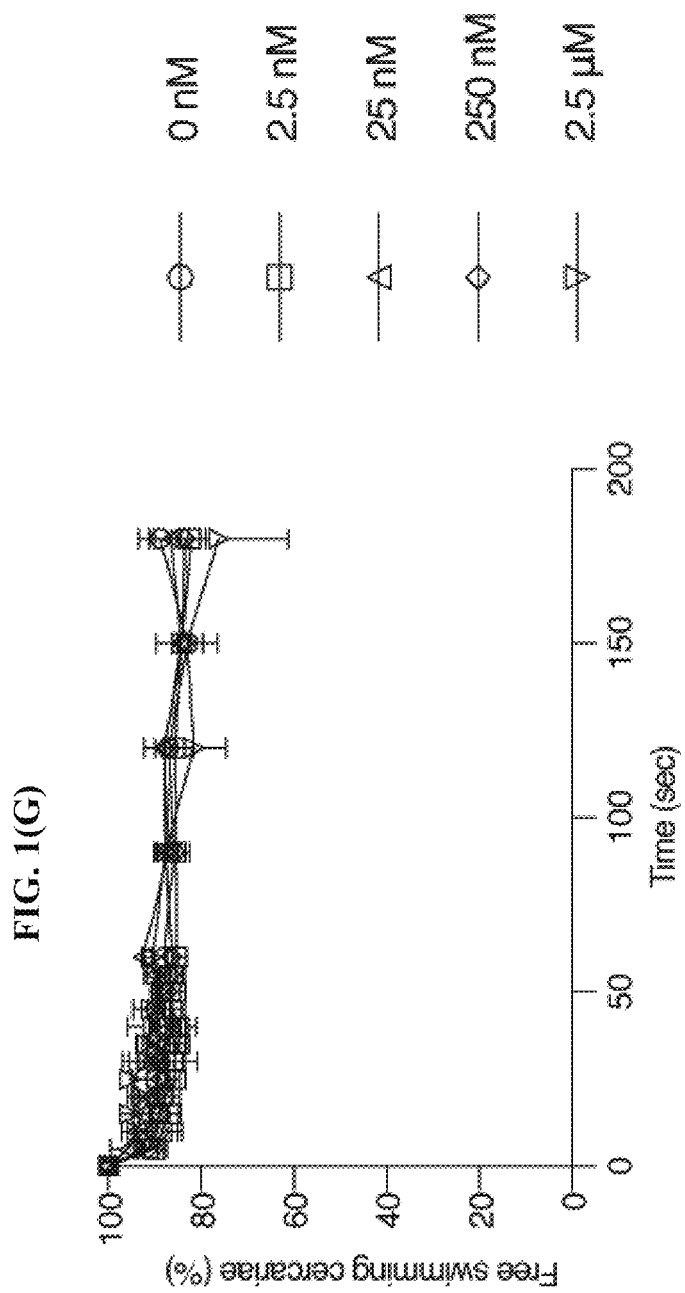
FIG. 1(G) shows the percentage of cercariae (~50) continuing to swim over three minutes after addition of epi-Ht-13-A at the specified final concentrations, according to the Examples. Triplicates were performed. Data are mean±S.D.
Figure 1G:
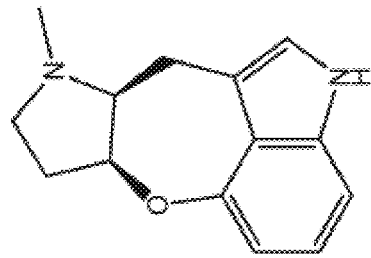

Org. Chem., 2015, 80:4783-4790). To test whether this common tetracyclic chemical scaffold is responsible for the paralytic effect, cercarial paralysis assays were performed using Ht-13-A and Ht-13-B, as well as three Ht-13-A derivatives and one epimer. Interestingly, Ht-13-A, although not as potent as SPF, had a paralytic effect on cercariae (FIG. 1(B)). In contrast, Ht-13-B could not paralyze cercariae, suggesting that the extra methyl group disrupts its interaction with the target molecule (FIG. 1(C)). Of the three Ht-13-A analogs, Ht-13-A-pr was the only compound that could efficiently paralyze cercariae and was at least 10-fold more potent than Ht-13-A, suggesting that the size or chemical property of the side chain is very important for proper interaction with the target (FIG. 1(D)-1(F)). In contrast to Ht-13-A, the epimer was unable to paralyze cercariae (FIG. 1(G)). This result further supports the suggestion that the configuration of SPF at C12, 13 is likely to be (R, S).

Accordingly, these results demonstrate that the compounds or pharmaceutical compositions of the present technology are useful in methods for preventing schistosomiasis and/or swimmer's itch in a subject in need thereof.

Example 6: Assessment of In Vivo Response to SPF and Analogs

Figure 2A:
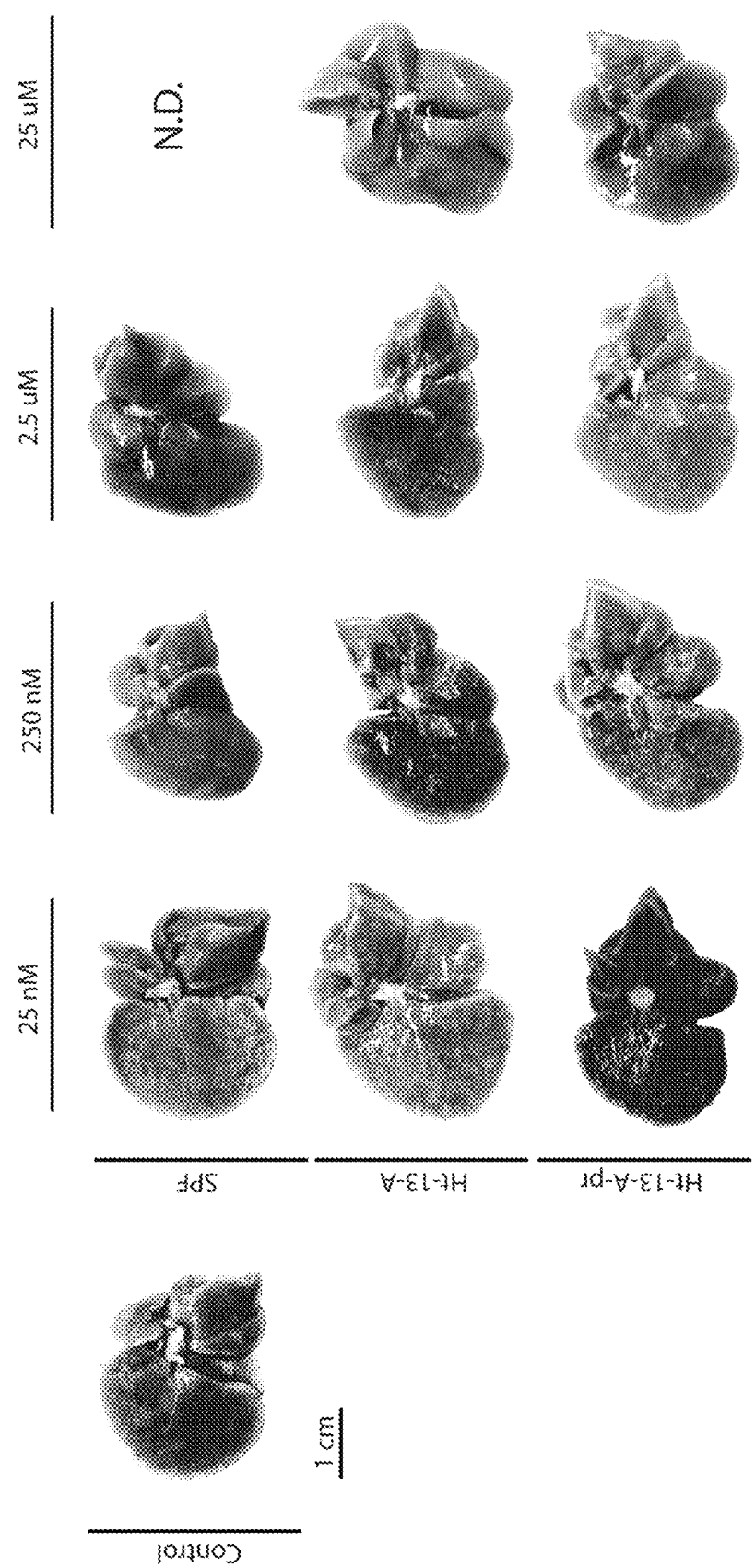
FIG. 2(A) shows representative livers (post perfusion) from mice infected with drug-treated cercariae, according to the Examples. The drugs tested were SPF, Ht-13-A, and Ht-13-A-pr. Livers in control mice and mice treated with lower concentrations of drug were darker in color and contained more granulomas (white spots). At higher concentrations of drug treatment, livers had normal morphologies with few or no granulomas. 25 μM SPF treatment was not determined (N.D.) due to the limited amount of SPF purified.
Figure 2B:
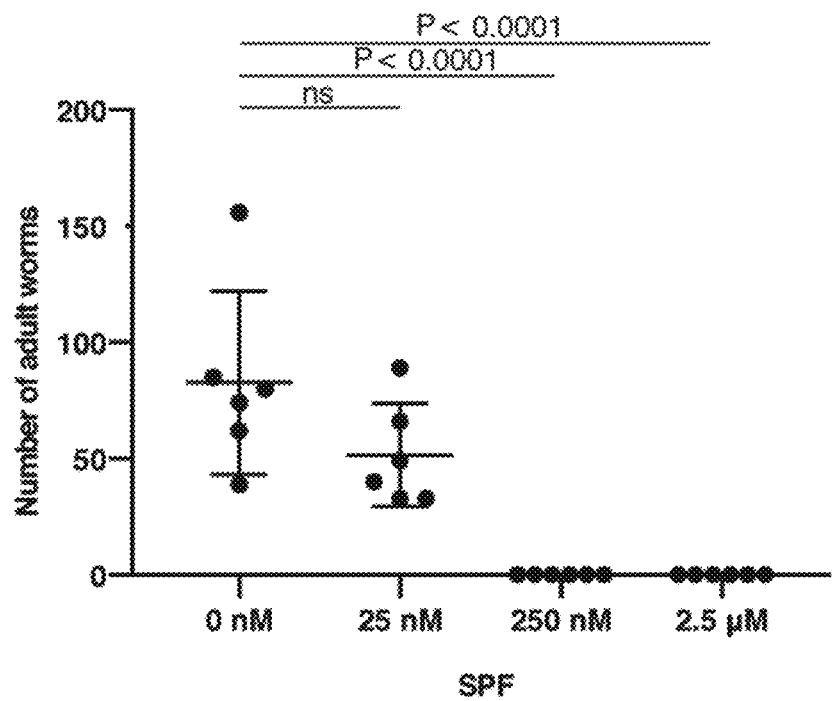
FIG. 2(B) shows the number of adult worms recovered from infected mice (6 mice total at each concentration of SPF), according to the Examples. Data are mean±S.D. Statistics: One-way ANOVA, post Dunnett's test.
Figure 2C:
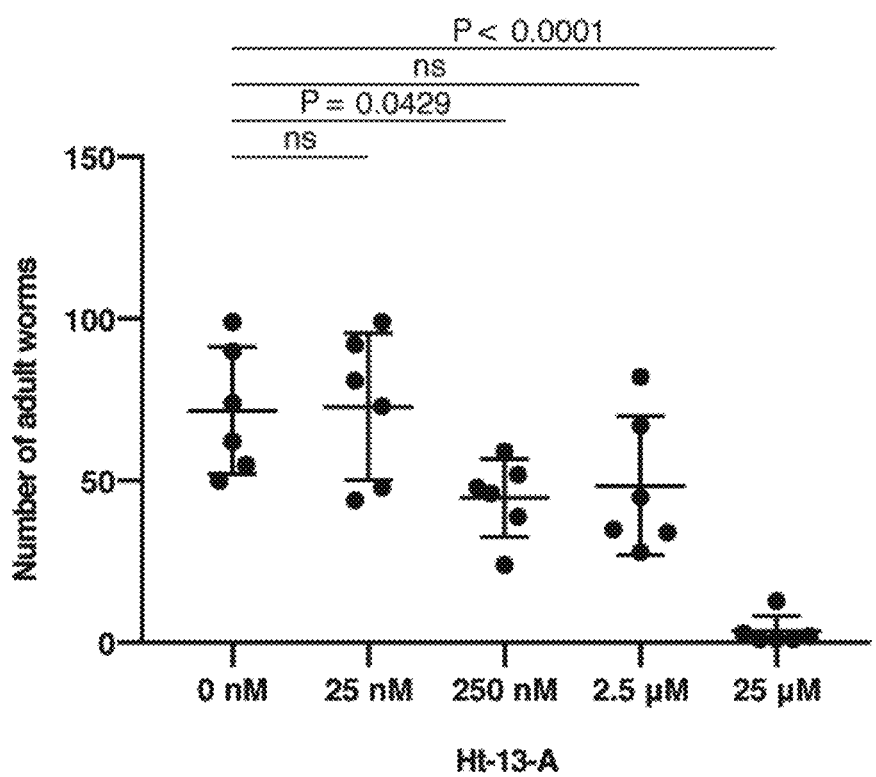
FIG. 2(C) shows the number of adult worms recovered from infected mice (6 mice total at each concentration of Ht-13-A), according to the Examples. Data are mean±S.D. Statistics: One-way ANOVA, post Dunnett's test.
Figure 2D:
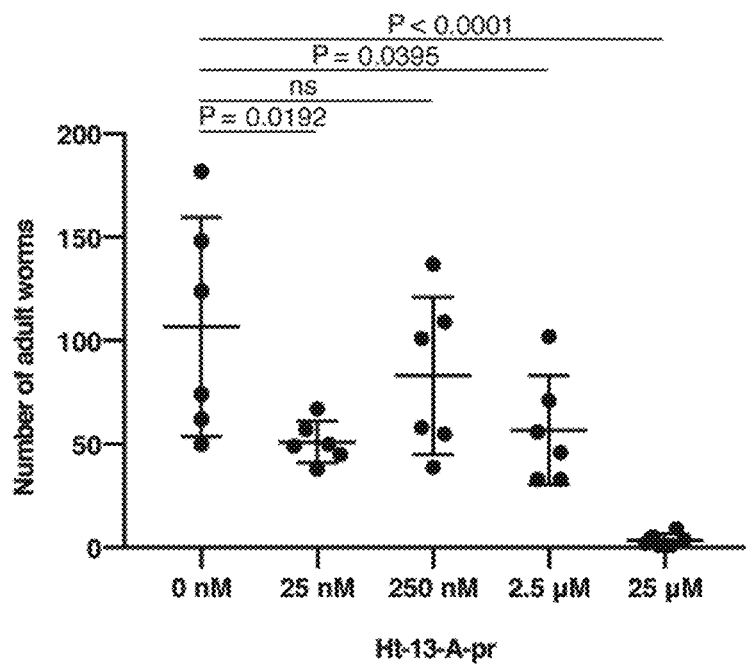
FIG. 2(D) shows the number of adult worms recovered from infected mice (6 mice total at each concentration of Ht-13-A-pr), according to the Examples. Data are mean±S.D. Statistics: One-way ANOVA, post Dunnett's test.
Figure 2E:
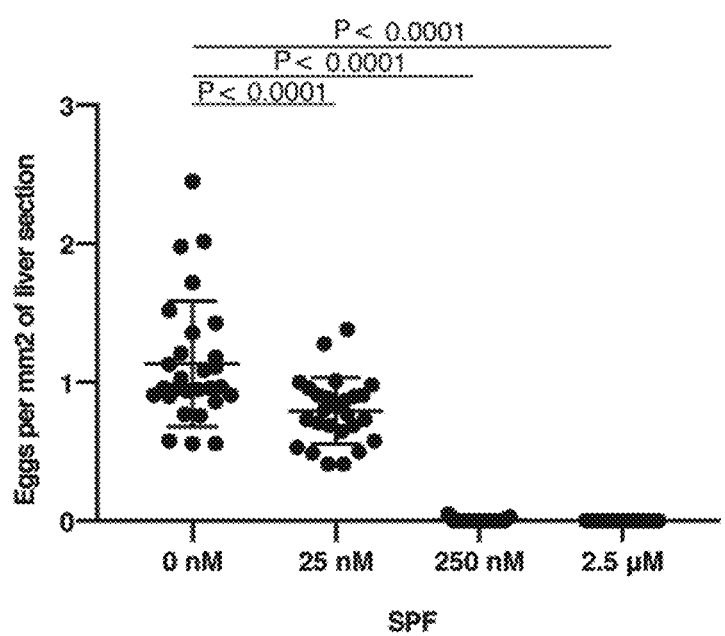
FIG. 2(E) shows the number of schistosome eggs recovered at each concentration of SPF per area ($/mm^2$) of liver sections (4-6 sections per mouse), according to the Examples. Data are mean±S.D. Statistics: One-way ANOVA, post Dunnett's test.
Figure 2F:
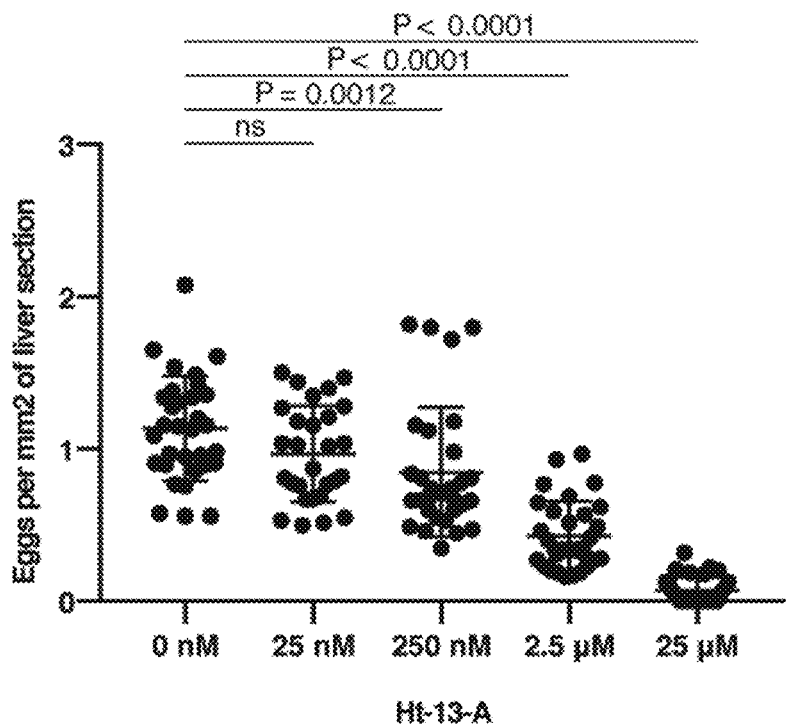
FIG. 2(F) shows the number of schistosome eggs recovered at each concentration of Ht-13-A per area ($/mm^2$) of liver sections (4-6 sections per mouse), according to the Examples. Data are mean±S.D. Statistics: One-way ANOVA, post Dunnett's test.
Figure 2G:
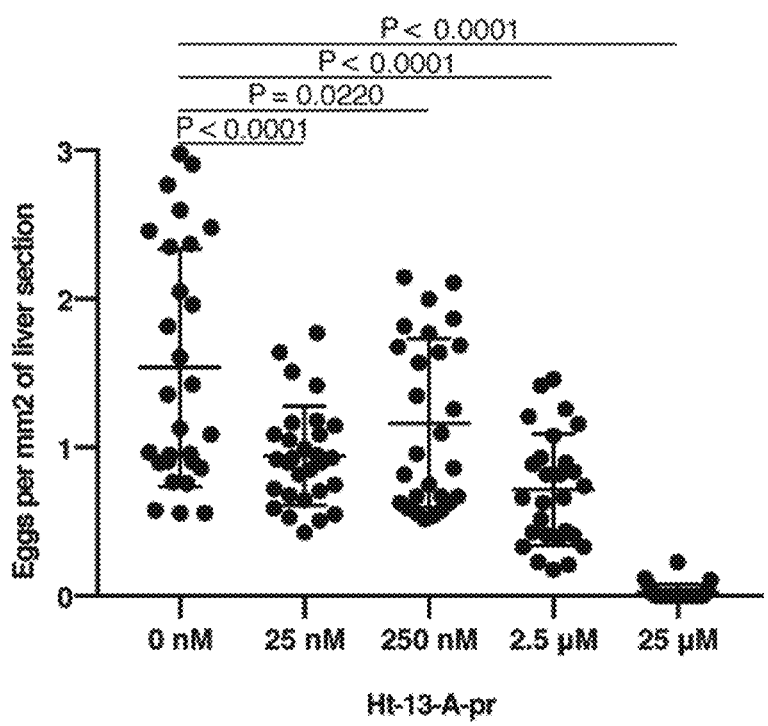
FIG. 2(G) shows the number of schistosome eggs per recovered at each concentration of Ht-13-A-pr per area ($/mm^2$) of liver sections (4-6 sections per mouse), according to the Examples. Data are mean±S.D. Statistics: One-way ANOVA, post Dunnett's test.

To determine if SPF-induced paralysis could prevent infection, ~200 cercariae were treated with different concentrations of SPF (25 nM, 250 nM, and 2.5 µM) for 10 min followed by a 30 min mouse tail infection (N=6 for each condition). Six-weeks post infection, the mice were euthanized, hepatic portal vein perfusion was performed, recovered schistosomes were counted, and mouse liver pathology was examined. In the control group, 83 adult worms were recovered on average (FIG. 2(A)). Livers from these mice appeared dark in color and had extensive granuloma formation (FIG. 2(A)). In contrast, no adult worms could be recovered from mice in the 250 nM or 2.5 µM SPF treatment group (FIG. 2(B)) and no granulomas were observed (FIG. 2(A)). Examination of histological sections further confirmed these livers were clear of schistosome eggs (FIG. 2(E)), suggesting a complete inhibition of infection. These data are consistent with observations that 250 nM or 2.5 µM SPF lead to full paralysis of the schistosomes (FIG. 1(A)). The data demonstrate that 25 nM SPF could paralyze most cercariae in vitro, however, the effects on mouse infection were not as severe (FIG. 2(A)). Without wishing to be bound by theory, it is possible that mechanical and/or chemical stimuli from mouse tails may overcome the SPF-induced paralytic effects at low SPF concentrations. According to the in vitro cercarial paralysis assays, Ht-13-A-pr had a potency that was of the same order of magnitude compared to SPF (FIG. 1(D)), however, neither 250 nM nor 2.5 µM Ht-13-A-pr blocked infection. Even higher concentrations (25 µM) of Ht-13-A or Ht-13-A-pr did not block infection as completely as SPF at 250 nM (FIG. 2(A), 2(C)-2(D), 2(F)-2(G)).

Accordingly, these results demonstrate that the compounds or pharmaceutical compositions of the present technology are useful in methods for preventing schistosomiasis and/or swimmer's itch in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions, or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A method of preventing schistosomiasis, comprising administering to a subject at risk of schistosomiasis infection, an effective amount of a compound of Formula I,

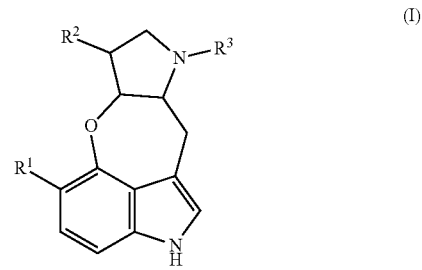

or stereoisomer, tautomer, and/or a pharmaceutically acceptable salt thereof, wherein
$R^1$ is H, OH, or $C_1$-$C_3$ alkoxy;
$R^2$ is H or $C_1$-$C_3$ alkyl; and
$R^3$ is H or $C_1$-$C_3$ alkyl.

2. The method of claim 1, wherein the compound has a purity of at least about 90%.

3. The method of claim 1, wherein the effective amount of the compound is about 25 nM to about 250 µM.

4. The method of claim 1, wherein the infection is caused by *Schistosoma haematobium, Schistosoma intercalatum, Schistosoma japonicum, Schistosoma mansoni, Schistosoma mekongi*, or a combination of any two or more thereof.

5. The method of claim 1, wherein the method further comprises sequentially, simultaneously, or separately administering to the subject, an effective amount of praziquantel.

6. The method of claim 1, wherein the subject is a human.

7. A method of preventing swimmer's itch, comprising administering to a subject at risk of contracting swimmer's itch, an effective amount of a compound of Formula I,

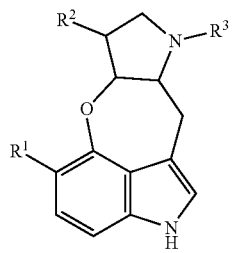

(I)

or stereoisomer, tautomer, and/or a pharmaceutically acceptable salt thereof, wherein $R^1$ is H, OH, or $C_1$-$C_3$ alkoxy;

$R^2$ is H or $C_1$-$C_3$ alkyl; and $R^3$ is H or $C_1$-$C_3$ alkyl.

8. The method of claim 7, wherein the compound has a purity of at least about 90%.

9. The method of claim 7, wherein the effective amount of the compound is about 25 nM to about 250 μM.

10. The method of claim 7, wherein the swimmer's itch is caused by *Trichobilharzia physellae* or *Trichobilharzia stagnicolae*.

11. The method of claim 7, wherein the subject is a human.

* * * * *